United States Patent
Karonis et al.

(10) Patent No.: US 8,766,180 B2
(45) Date of Patent: Jul. 1, 2014

(54) HIGH PERFORMANCE COMPUTING FOR THREE DIMENSIONAL PROTON COMPUTED TOMOGRAPHY (HPC-PCT)

(75) Inventors: Nicholas Karonis, West Chicago, IL (US); George Coutrakon, Redlands, CA (US); Kirk Duffin, Dekalb, IL (US); Bela Erdelyi, Romeoville, IL (US); Kevin Naglich, Elgin, IL (US); Scott Penfold, Adelaide (AU); Paul Rubinov, Batavia, IL (US); Victor Rykalin, Aurora, IL (US); Vishnu Zutshi, Dekalb, IL (US)

(73) Assignee: Board of Trustees of Northern Illinois University, Dekalb, IL (US)

( * ) Notice: Subject to any disclaimer, the term of this patent is extended or adjusted under 35 U.S.C. 154(b) by 0 days.

(21) Appl. No.: 13/638,314

(22) PCT Filed: Apr. 4, 2011

(86) PCT No.: PCT/US2011/031104
§ 371 (c)(1),
(2), (4) Date: Sep. 28, 2012

(87) PCT Pub. No.: WO2011/162851
PCT Pub. Date: Dec. 29, 2011

(65) Prior Publication Data
US 2013/0015352 A1 Jan. 17, 2013

Related U.S. Application Data

(60) Provisional application No. 61/320,542, filed on Apr. 2, 2010.

(51) Int. Cl.
*G01T 1/20* (2006.01)

(52) U.S. Cl.
CPC .......................................... *G01T 1/20* (2013.01)
USPC ........................ 250/306; 250/307; 250/370.09

(58) Field of Classification Search
USPC ..................... 250/306, 307, 370.09
See application file for complete search history.

(56) References Cited

U.S. PATENT DOCUMENTS

| | | | |
|---|---|---|---|
| 6,078,052 A | 6/2000 | Difilippo | |
| 6,635,877 B2 | 10/2003 | Kusuyama et al. | |
| 7,345,284 B2 * | 3/2008 | Tumer | 250/370.09 |
| 2007/0040830 A1 | 2/2007 | Papageorgiou | |
| 2007/0045547 A1 | 3/2007 | Tumer | |
| 2009/0134334 A1 | 5/2009 | Nelson | |
| 2011/0220794 A1 * | 9/2011 | Censor et al. | 250/307 |
| 2012/0273665 A1 * | 11/2012 | Schulte et al. | 250/252.1 |

OTHER PUBLICATIONS

Search Report and Written Opinion issued in Int'l App. No. PCT/US2011/031104 (2011).

* cited by examiner

*Primary Examiner* — Kiet T Nguyen
(74) *Attorney, Agent, or Firm* — Barnes & Thornburg LLP; Alice O. Martin

(57) ABSTRACT

A proton computed tomography (pCT) detector system, including two tracking detectors in sequence on a first side of an object to be imaged, two tracking detectors in sequence on an opposite side of the object to be imaged, a calorimeter, and a computer cluster, wherein the tracking detectors include plastic scintillation fibers. All fibers in the detector system are read out by Silicon Photomultipliers (SiPM). A method of imaging an object by emitting protons from a source through two tracking detectors, through and around the object, and through two opposite tracking detectors, detecting energy of the protons with a calorimeter, and imaging the object.

25 Claims, 9 Drawing Sheets

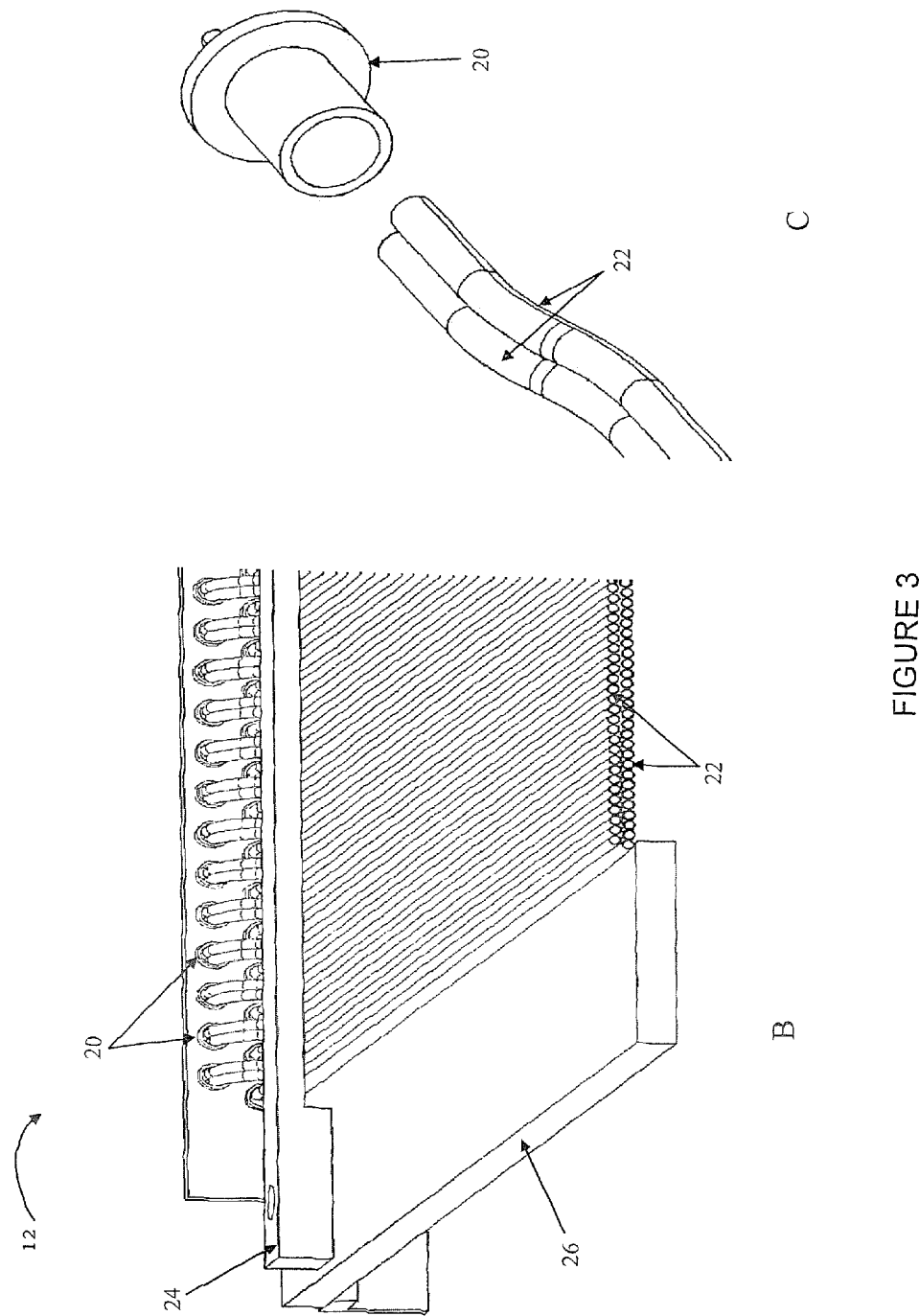

HIGH PERFORMANCE COMPUTING FOR THREE DIMENSIONAL PROTON COMPUTED TOMOGRAPHY (HPC-PCT)

CROSS REFERENCE TO RELATED APPLICATIONS

This application is a U.S. nationalization under 35 U.S.C. §371 of International Application No. PCT/US2011/031104, filed Apr. 4, 2011, which claims priority to U.S. provisional patent application No. 61/320,542, filed Apr. 2, 2010. The disclosures set forth in the referenced applications are incorporated herein by reference in their entireties, including all information as originally submitted to the United States Patent and Trademark Office.

GRANT INFORMATION

Research in this application was supported in part by a grant from the Department of Army USA Medical Research Mat Command (Grant No. W81XWH-10-1-0170). The Government has certain rights in the invention.

BACKGROUND OF THE INVENTION

1. Technical Field

The present invention relates to three-dimensional computing. In particular, the present invention relates to proton-computed tomography.

2. Background Art

Generating an internal 3D image of an object with proton computed tomography (pCT) starts by firing many protons through the object. Each proton's path (i.e., trace history) is recorded and the collection of all the trace histories are used as input to a computer program that generates the image. Some posit that images generated through pCT will be more effective in proton-based treatments of cancer than images produced through X-rays.

The algorithms that produce images from proton trace histories are complex and involve many stages. The computer memory and speed needed to produce a quality 3D image of an object for which proton-based cancer treatment can be applied (e.g., a human head or pelvis) within clinically meaningful time frames exceeds the capacity of even the most powerful desktop computers available today. Therefore, there is a need for an algorithm to make images from proton trace histories more effectively.

Detectors for pCT in the prior art employ larger bulky plastic cube shaped tubes (such as in Pemler, et al.) with large and bulky photon sensors that require much larger volumes that present problems when mounted on a proton gantry with limited space around the patient. Pemler, et al. describes the possibility to perform radiography with protons and used a single X-Y plane in front of the object being analyzed and a single X-Y plane after. Pemler, et al. also uses vacuum photomultipliers, square fibers, and combinatorial readout. Amaldi, et al. describes a Proton Range Radiography system with an imaging area of 10 cm×10 cm with a stack of thirty thin plastic scintillators. The current pCT detector at Loma Linda uses silicon wafers that are limited in available area (9 cm×9 cm), thus requiring a mosaic of overlapping tiles to achieve large area (27×36 cm). The maximum size now produced of silicon wafers is 10 cm×10 cm. The tiles are shingle overlapped or placed with edges butting, which create dead space in the detector or double layers that require "mathematical removal" during image calculations.

Therefore, there also remains a need for a detector for pCT that eliminates dead space and double layers created by the arrangement of tiles.

SUMMARY OF THE INVENTION

The present invention provides for a proton computed tomography (pCT) detector system, including two tracking (2D) detectors in sequence on a first side of an object to be imaged, two tracking (2D) detectors in sequence on an opposite side of the object to be imaged, and a calorimeter, wherein the tracking detectors include plastic scintillation fibers.

The present invention also provides for a method of imaging an object by emitting protons from a source through two tracking detectors, through and around the object, and through two opposite tracking detectors, detecting energy of the protons with a calorimeter, and imaging the object.

DESCRIPTION OF THE DRAWINGS

Other advantages of the present invention are readily appreciated as the same becomes better understood by reference to the following detailed description when considered in connection with the accompanying drawings wherein:

FIGS. 3A-3C are three-dimensional representations of one plane of the tracking detector of the present invention;

DETAILED DESCRIPTION OF THE INVENTION

Figure 1:
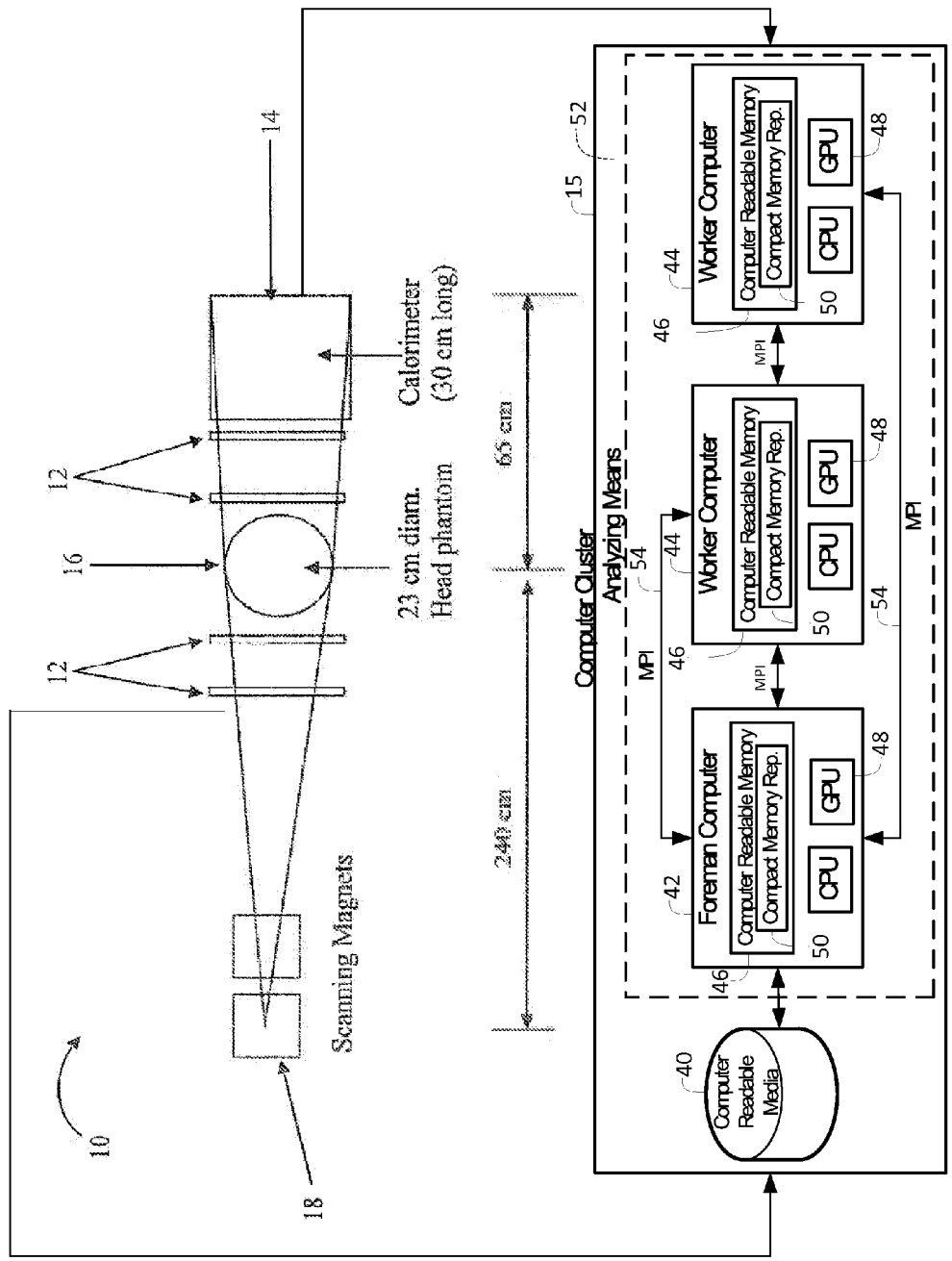
FIG. 1 is a layout of the pCT detector system of the present invention.

The present invention provides for a pCT detector system 10, shown generally in FIG. 1, for generating 3D images from proton trace histories. The pCT detector system 10 preferably includes four tracking detectors 12, a calorimeter 14, and a computer cluster 15.

The tracking detectors 12 are used to detect the coordinates in the X and Y plane of the protons. Each detector 12 has two planes, an X plane and a Y plane, with the fibers (strips) oriented in the appropriate direction for X and Y measurements of the proton tracks. Each detector is fabricated by placing one X and one Y plane in close proximity with a thin foam-like material in between.

There are preferably four tracking detectors 12 arranged around the object 16 to be imaged, two on one side of the object 16 and two on the opposite side of the object 16. This arrangement is further described below. There can also be more than two tracking detectors 12 on each side of the object 16 in order to create redundancy. The tracking detectors 12 include 1 mm diameter thin circular plastic scintillation fibers 22, closely packed in a row, and covering the full area of the imaging field, preferably 27 cm by 36 cm, or 18 cm.times.36 cm. The tracking detectors 12 can be any other suitable size. The core of the fibers is preferably polystyrene with cladding of PMMA (Poly(methyl methacrylate)). The tracking detectors 12 also include appropriate electronics in order to detect the position of the protons and relay this data to the computer cluster 15.

The use of scintillation fibers for proton imaging has been reported in the prior art, but the tracking detectors 12 of the present invention offer higher spatial resolution and larger area coverage than previous detectors and eliminate the tile construction of the prior art. Up to six meters can be covered with these plastic scintillating fibers 22 without dead area. The smaller circular fibers 22 produce better resolution to sub-millimeter level over the larger square tubes used in prior art devices. One crucial difference between the present invention and the prior art is the use of SiPM (or solid state photomultiplier) 20 while reading out scintillating fibers 22. Previous devices were based on using bulky vacuum photomultipliers with poor light sensitivity in green diapazon of the light spectrum. The prior art used thick square scintillating fibers in order to increase light output. The tracking detectors 12 of the present invention use SiPM 20 with as much as two time higher light sensitivity and allows for use of thinner fibers 22.

Figure 2:
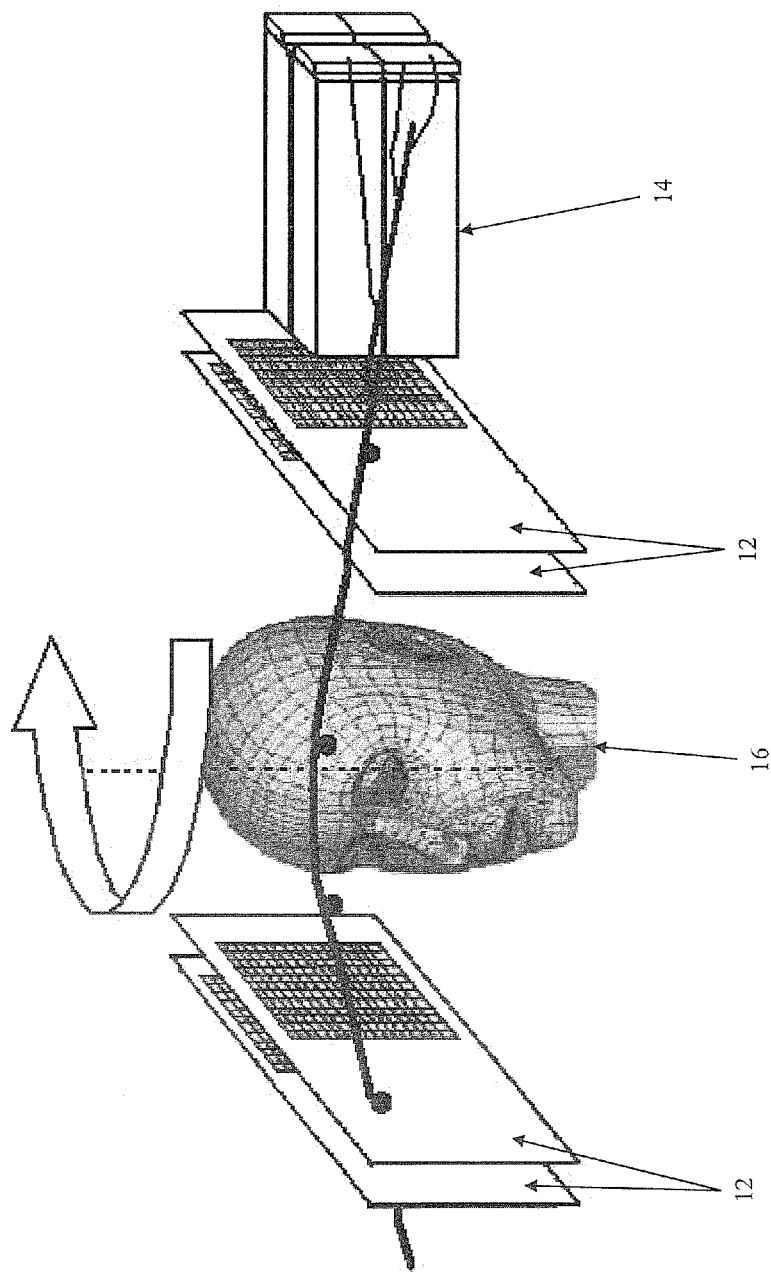
FIG. 2 is a three-dimensional representation of the pCT detector system core idea of the present invention.

The tracking detectors 12 are arranged so that two are placed in sequence on a first side of an object 16 to be imaged and two are placed in sequence on an opposite side of the object 16, as shown in FIGS. 1 and 2. Scanning magnets (or a source) 18 that emit the proton beams of the system 10 are located at a position opposite to the calorimeter 14 on either side of the outer tracking detectors 12. For example, the scanning magnets 18 can be located 240 cm from the center of the object 16, and the calorimeter 14 can be 65 cm from the center of the object 16. The inner tracking detectors 12 can be 15 cm from the center of the object 16 and the outer tracking detectors 12 can be 30 cm from the center of the object 16. Other distances can be used as appropriate.

Figure 3A:
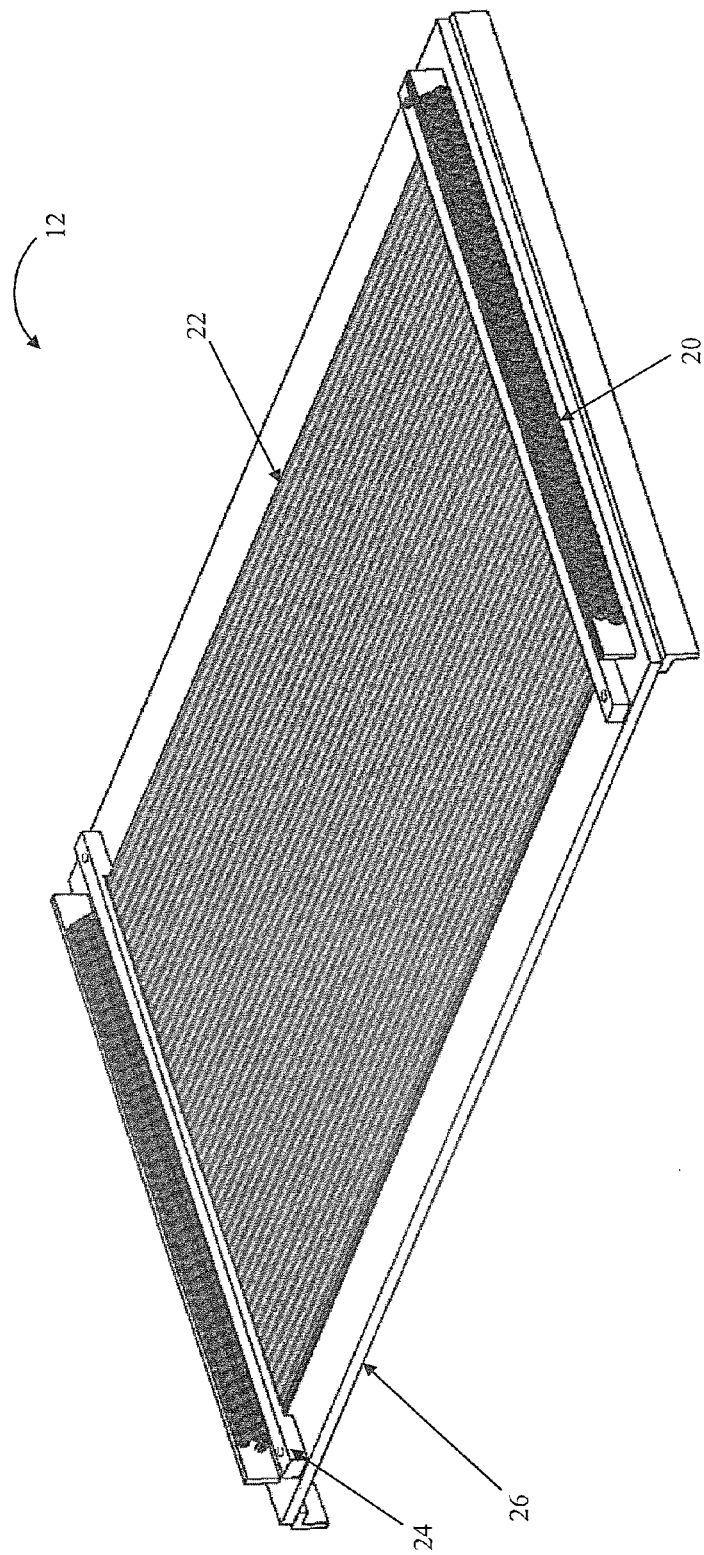
Figure 7:
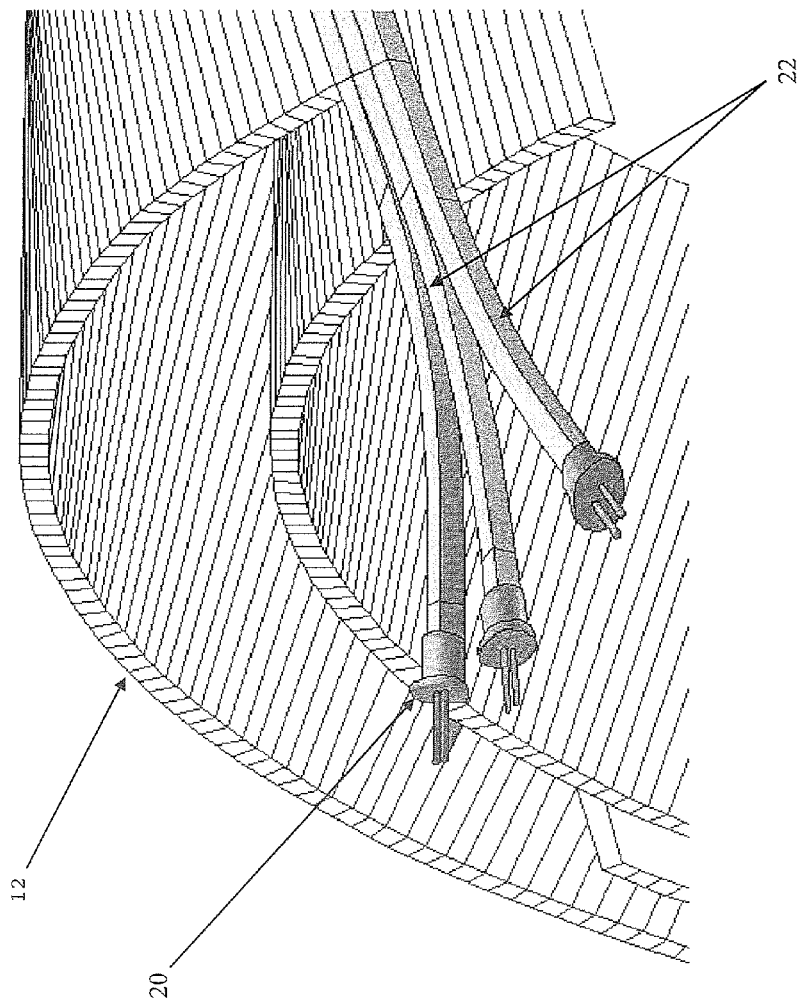
FIG. 7 is a perspective view of fibers of the tracking detector.

The tracking detectors 12 include the use of low cost Silicon Photomultipliers (SiPM) 20 attached to the plastic scintillating fibers 22 for signal amplification in lieu of phototubes as used in the prior art, as shown in FIGS. 3A-3C. The SiPMs 20 provide continuous coverage and remove the tile construction effect. SiPMs are unaffected by magnetics contrary to phototubes. SiPMs have been historically used in particle detectors. SiPMs are intrinsically fast, of order 100 nanosecond resolving time between events. Therefore, this design allows much higher data acquisition rates than previous detector systems. The plastic scintillating fibers 22 can have a cross-sectional shape of a square (shown in FIG. 7), circle, or hexagon. The tracking detectors 12 with SiPMs 20 can include two scintillating fibers 22 simultaneously, alternatively, one fiber 22 can be used for one SiPM 20. Preferably, the fiber 22 diameter is in the range of 0.75 mm-1 mm. The fibers 22 can be polystyrene scintillating fibers that produce light when protons cross their thickness. Two layers of fibers 22 increase detection efficiency in contrast to one layer. Another orthogonal double layer of fibers 22 can be included in order to have a 2D coordinate of the protons in space. As shown in FIGS. 3A-3B, the tracking detectors can include a mechanical support 24 for the SiPM, as well as a Rohacell support 26 that serves as a support for scintillating fiber 22 placing. Any other supports can be used as known in the art in order to create the tracking detectors 12.

In one example of a tracking detector 12, the area of 27×36 $cm^2$ (tracking part) is covered. If the picked diameter of the scintillating fiber 22 is 1 mm then 270 fibers, 270 SiPMs, and 270 channels of electronics are needed. This is true for a one projection only (X). The 2D plane includes X and Y projections (270+360=630 channels). The total tracking detector 12 includes approximately 630×4=2520 channels.

Figure 6:
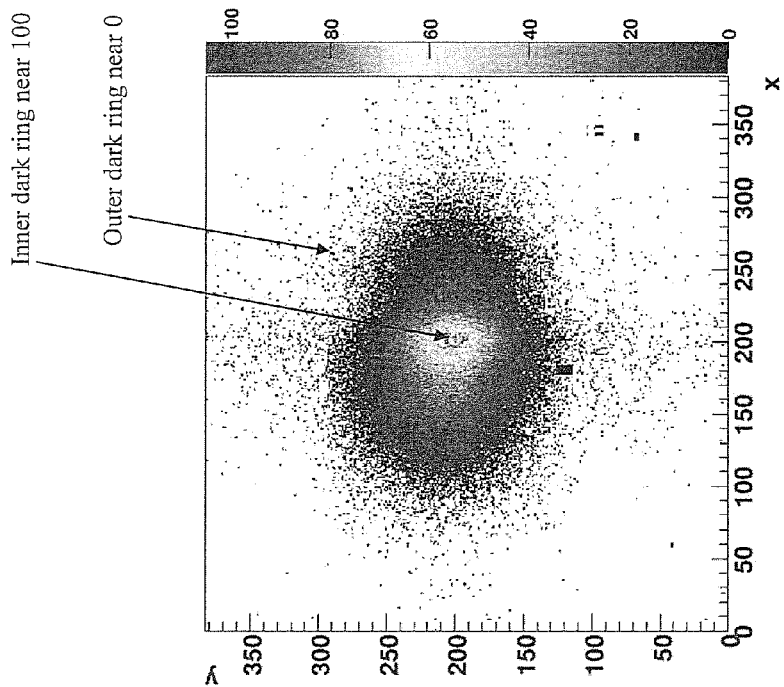
FIG. 6A is a front view of a silicon strip detector.
FIG. 6B is a graph of a proton beam detected.
Figure 6:
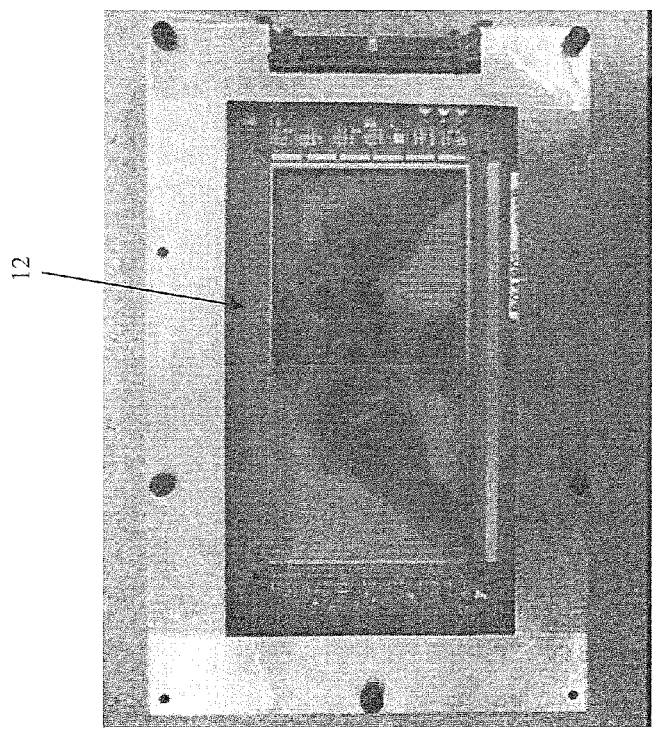

FIG. 6A shows a side view of the tracking detector 12 of the present invention. In this detector 12, there are two layers of silicon strips. The silicon sensors which connect to the SiPms 20 are 89.5 mm×89.5 mm with a strip pitch of 238 μm and 400 μm thickness. The strips of each layer are individually connected to six ASICs*64 strips. FIG. 6B shows a view of a proton beam detected by the tracking detector 12 with X and Y coordinates.

Figure 8:
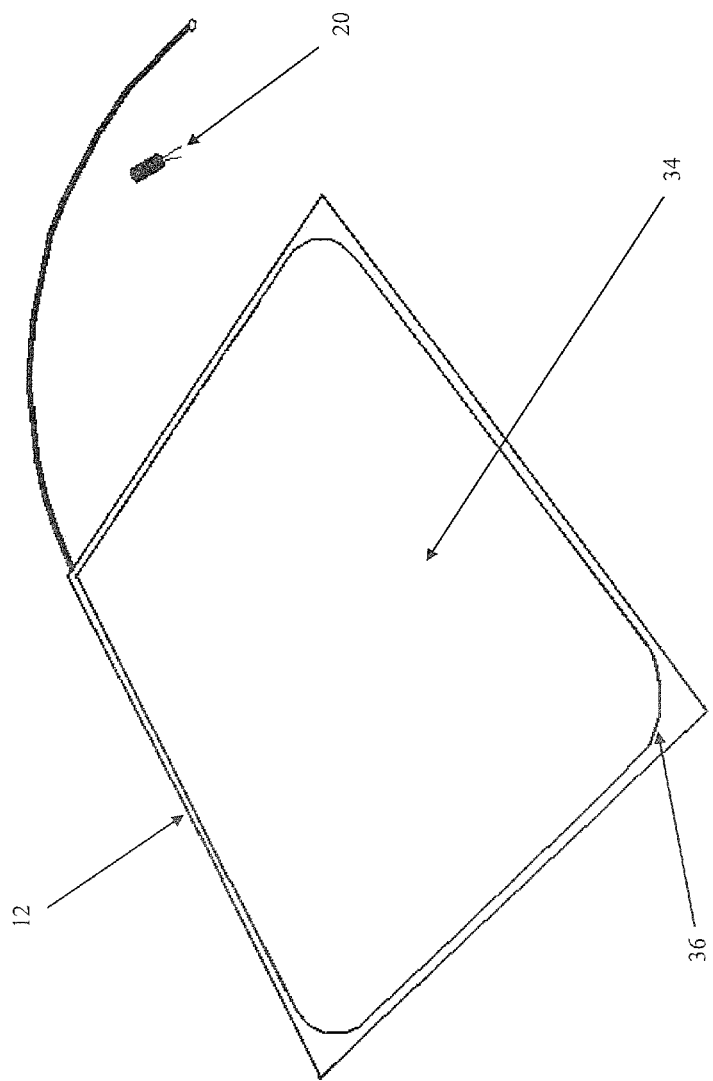
FIG. 8 is perspective view of a scintillating plate as part of the calorimeter.

The calorimeter 14 is used to detect proton energy that is emitted from the source 18. SiPM 20 with a diameter of 1.2 mm, can provide a readout (digital or analog) through 1.2 mm wavelength shifter (WLS) fibers 36. The SiPM 20 used in the calorimeter 14 can be the same type as used in the tracking detectors 12. The calorimeter 14 can be arranged in a stack (at least two) of 3 mm scintillator plates 34, as shown in FIG. 8. In this case, the total number of channels are about 120. This is arrived at by the following. One scintillating plate 34 includes 1 WLS fiber and 1 SiPM. The total number of plates is 120. So, there are 120 plates, 120 WLS fibers, 120 SIPM, and 120 channels of electronics (120 channels). The calorimeter 14 can further include appropriate electronics to relay data to the computer cluster 15.

In prior art devices (Amaldi, Premier), different combinations of readout systems were used. There has never before been the use of SiPM and scintillator fibers and SiPM and WLS fibers in combination. Amaldi, et al. used SiPM and WLS fibers for the calorimeter readout, but gas photomultipliers were used as a tracking detector. Premier, et al. used vacuum photomultipliers to readout scintillating fibers and vacuum photomultipliers to readout the calorimeter. In both mentioned cases, the targeted system name was a radiograph whereas the present invention is a 3D tomograph.

Figure 4:
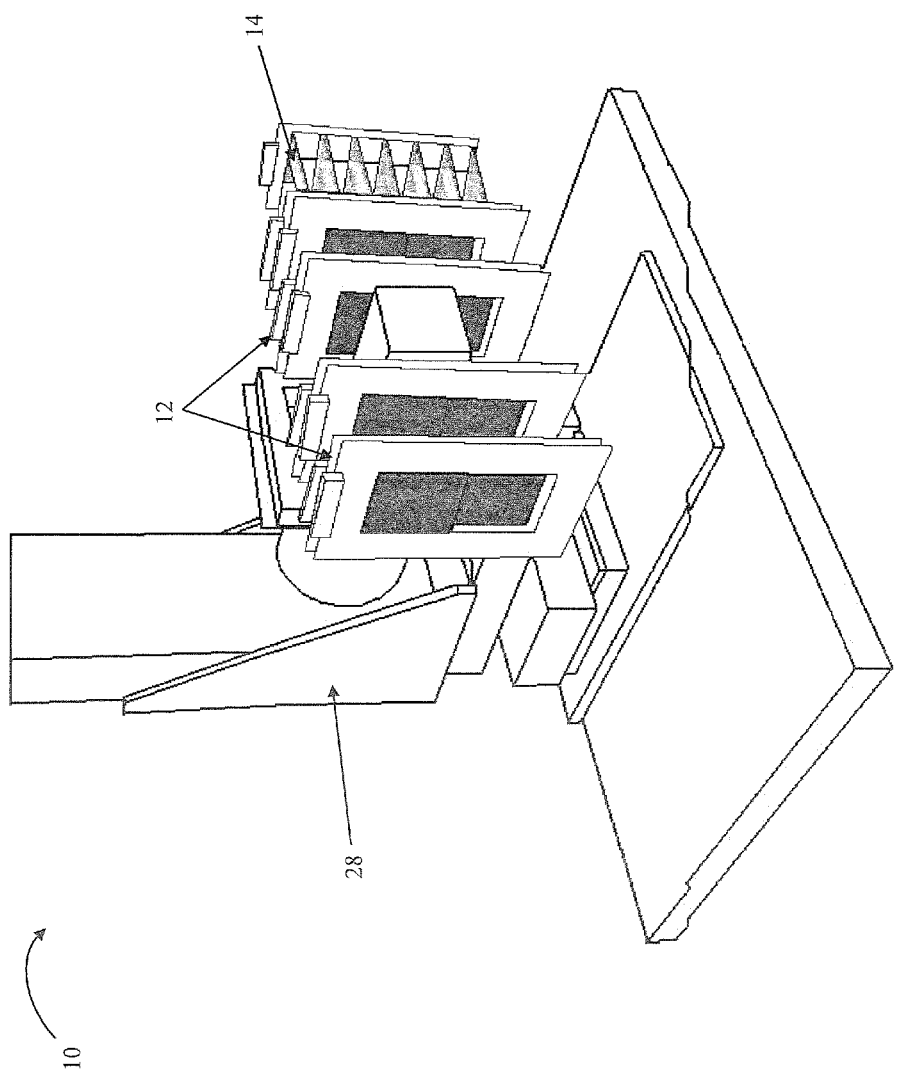
FIG. 4 is a three-dimensional representation of the system of the present invention.

FIG. 4 shows the system 10 with a rotational stage 28 that holds and rotates an object 16 during proton exposition.

Unique features of this detector include large area coverage without dead zones or overlapping detectors that can produce artifacts in the reconstructed images. This solution offers better signal to noise than a previous approach that uses silicon strip detectors. Thus, scintillation fibers attached to silicon photo multipliers reduce background noise to produce cleaner images and lower dose to the patient for imaging. This is the first pCT detector to record protons at a rate of 2 million per second and reduce imaging time to less than 10 minutes, an acceptable time for patient imaging.

The present invention provides for a method of imaging an object by emitting protons from a source through two tracking detectors, through and around the object, and though two opposite tracking detectors, detecting the protons with a calorimeter, and imaging the object.

More specifically, protons are emitted from a source 18 (scanning magnets) through two tracking detectors 12, through and around the object 16 to be imaged, through additional two tracking detectors 12, and finally pass through the energy detector (i.e., calorimeter 14) (FIG. 1). Protons of sufficient energy can penetrate the human body and can be tracked upon entry and exit of the tracking detectors 12. The X and Y position of the protons are measured and detected on the X and Y planes of each of the tracking detectors 12. Preferably, the system 10 includes 4 detectors or eight planes of these fiber trackers to record the position of each proton track as it passes through each plane. The object 16 being imaged is located such that two detectors 12 are on each side of the image. The detectors 12 rotate about the object 360 degrees during operation.

Generating 3D proton computed tomography images requires data from a large number of proton histories to be stored in memory. Previous computer programs executed on stand-alone general purpose graphical processing unit (GPGPU) workstations implemented in prior art were constrained by the demand on computer memory. The approach described here is not limited to demands on computer memory in the same manner as the reconstruction is executed on multiple workstations simultaneously.

The resulting data recorded from the detector and the calorimeter can be fed into an image reconstruction software program on a computer cluster to allow high-resolution images to be formed in under 10 minutes after irradiation.

The computer program is written in terms of the Message Passing Interface (MPI) standard 54. Writing the program in terms of the MPI standard enables one to run the program on a cluster of many computers as opposed to a single computer. The program can be run on approximately 768 CPUs (computers) plus 96 GPUs (graphic processing units) 48. In this way, it is possible to bring to bear the combined memory and computational power of many computers at one time, thus substantially reducing the time it takes to run the program (by orders of magnitude) as well as increasing the problem size (as measured by size of image space and the sharpness of the image) the program can image. Therefore, data acquired from the calorimeter 14 can be analyzed on a cluster of multiple computers with this standard.

A compact way was also developed in which to store in the computer's memory the information needed to generate the image. This compact design reduces the memory required to solve the problem by orders of magnitude. Previous computer programs implemented in the prior art, which executed on stand-alone workstations, were constrained by the amount of computer memory their programs required.

By contrast the compact memory representation 50 enables one to deploy the computer program to solve the entire 3D image space at one time. This results in images of higher quality as it allows one to use the information from the trace histories of more protons as compared to the "slice and assemble" technique used in the prior art.

The new computer program of the present invention is capable of producing high-quality 3D internal images for cancer patients being treated with proton therapy. Most notably, the new computer program, and specifically the two novel techniques of adding MPI and the compact memory representation, is able to produce quality images faster than any other known methods and, in fact, so fast (i.e., less than 10 minutes) that the program can not only be used to augment or replace X-ray generated images used in proton treatment of cancer today, but medical care providers can find new uses for such images to improve the quality of care delivered to the patient (e.g., just before treating the patient with proton therapy generate one more set of images to refine the treatment plan). pCT imaging and this new computer program can become the state of the art, and thus become the de facto standard, for generating images for every cancer patient globally treated with proton therapy.

The computer program is further described in Example 1 below, and an example of code is shown in EXAMPLE 2. Briefly, a foreman computer 42 distributes equal amounts of proton histories to multiple worker computers 44 and the foreman computer 42 itself. An Integrated Electron Density (IED) and Most Likely Path (MLP) are computed by each of the computers. A solution vector is solved for and stored on computer readable memory 46 in each of the computers. Copies of the solution vector from the worker computers 44 are sent to the foreman computer 42 and combined and stored on computer readable media 40. The combined solution vector is tested by the foreman computer 42, and if the combined solution vector is determined to be done, an image is then produced of the object. If it is determined that the combined solution vector is not done, the combined solution vector is transmitted to the worker computers 44, and each of the above steps are repeated until the combined solution vector is determined to be done by the foreman computer 42, and an image is produced of the object. In some embodiments, the foreman computer 42 and work computers 44 constitute an analyzing means 52.

Figure 5:
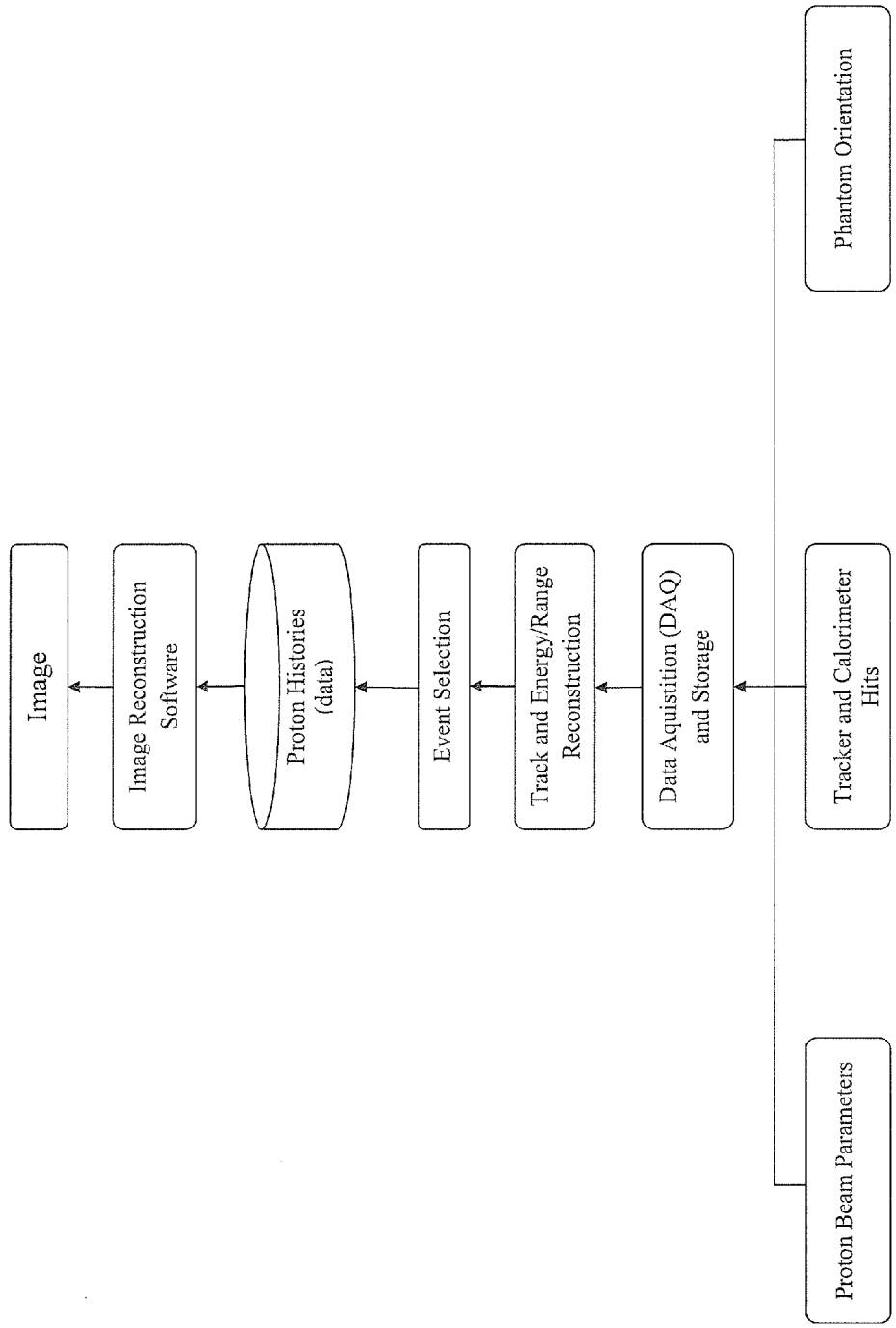
FIG. 5 is flow-chart showing the process of generating images with the scanner system.

FIG. 5 shows a flow chart of the general process of the present invention. The proton detection process is shown in the bottom row, and data from the tracking detectors 12 and calorimeter 14 is analyzed from the top using parallel processors and the algorithms described above. Finally, an image is generated, which looks generally like a CT image.

Thus, the advantages of this approach are that it significantly reduces both the time and memory, each by orders of magnitude, required to generate an image. These dramatic reductions in both time and space not only change how the images are produced, but also how they can be used in cancer therapy.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Memory and CPU Count Estimate for Block Methods March 2010

1 The Approach.

Our proposed solution to implement string averaging methods is to use MPI with set of worker processes where one worker is designated as the foreman. The foreman reads the proton histories and distributes them evenly across all the workers, saving an equal share for himself. From their portion of the histories each worker computes (one time only) IED and MLP and initializes their solution vector which represents the entire voxel space (i.e., each worker has its own copy of the entire solution).

The program then enters an iteration loop in which:
1. Each worker uses their IED and MLP to modify their copy of the solution. This is an iterative process with its own stopping criterion.
2. Each worker that is not the foreman sends their copy of the solution to the foreman.
3. The foreman collects and combines with his own the solution vectors from all the other workers and tests combined solution vector. If combined solution is "done", then foreman tells all the other workers to end. If "not done" the foreman broadcasts the combined solution vector to all the other workers who, in turn and along with the foreman, use that as their starting point for their next iteration.

2 Input Parameters

We define the following input parameters that characterize the imaging space and the computational resources.

Plane Detector Parameters $P_h$, $P_w$ height and width (e.g., in cm), respectively, of the plane detectors $P_r$ resolution of detector strips (e.g., 238µ)

Imaging Parameters $I_a$ number of discrete angles (360°) from which imaging protons are fired Voxel Space Parameters
$V_h$, $V_w$, $V_d$ height, width, and depth (e.g., in cm), respectively, of voxel space
$V_T$ desired resolution of image (e.g., 1 mm)
$V_S$ MLP image resolution oversample rate (e.g., 2)
$V_p$ protons per voxel; number of imaging protons travelling through each voxel Computational Resource Parameters
M memory per process
f number of bytes to store a single precision float
p number of bytes to store a pointer 3 Memory Contraint and Process Count In this section we compute the number of histories each worker can process, which we denote with $H_w$, as constrained the memory per process M, and from $H_w$ and the total number of histories determine the number processes will be required, denoted by P, to solve the problem.

Indices and Counting. We find a repeated need to compute the minimum number of bytes needed for counting and to also index various discretized spaces. For notational convenience we therefore define these terms V; the number of voxels in our voxel space,
$b_v$; the number of bytes needed to index the linearlized voxel space,
$b_{ph}$ and $b_{pw}$; the number of bytes needed to index dimensions $P_h$ and $P_w$, respectively, and
$b_{Ia}$; the number of bytes needed to index the discrete firing angles as follows:

$$V = \left\lceil \frac{V_h V_w V_d}{V_T^3} \right\rceil$$

$$b_v = \left\lceil \frac{\lceil \log_2 V \rceil}{8} \right\rceil$$

$$b_{ph} = \left\lceil \frac{\left\lceil \log_2 \frac{P_h}{P_T} \right\rceil}{8} \right\rceil$$

$$b_{pw} = \left\lceil \frac{\left\lceil \log_2 \frac{P_w}{P_T} \right\rceil}{8} \right\rceil$$

$$b_{Ia} = \left\lceil \frac{\lceil \log_2 I_a \rceil}{8} \right\rceil$$

Input. Each proton history is characterized by an 11-tuple comprised of four <z, y> tuples (one for each detector plane), input and output energies ($E_{in}$ and $E_{out}$), and a projection angle. These values require $b_{ph}+b_{pw}$ bytes of storage for each of the four <x, y> tuples plus three floats for the last three values. Each history is processed to determine the 3-D surface of the phantom (i.e., space carving). In this process the voxel space is represented by an array, one element for each voxel, and the elements of the array are set or cleared if the phantom does nor does not occupy the voxel, respectively. We choose initially to represent each voxel with a byte rather than a bit to reduce the time to access the array. Therefore, the memory ($I_m$) required to store the processed input projection histories for each worker is $$I_m = H_w[4(b_{ph} + b_{pw}) + 3f] + V \quad (1)$$

$$= H_w \left[ 4 \left( \left\lceil \frac{\left\lceil \log_2 \frac{P_h}{P_r} \right\rceil}{8} \right\rceil + \left\lceil \frac{\left\lceil \log_2 \frac{P_w}{P_r} \right\rceil}{8} \right\rceil \right) + 3f \right] + \left\lceil \frac{V_h V_w V_d}{V_r^3} \right\rceil$$

IED. Each proton history is used to compute an Integrated Electron Density (IED), which is stored as a float. The memory needed to store the IEDs ($IED_m$) for each worker is $$IED_m = H_w f \quad (2)$$

MLP. Each proton history is used to compute the proton's Most Likely Path (MLP) by identifying those voxels through which the proton passed. Assuming near-linear trajectories, the set of voxels "touched" by a single proton's path is very small compared to the total voxel space and so a sparse representation is appropriate. We choose initially to list each voxel in a proton's path by identifying the voxel by its index in the linearized voxel space (i.e., requiring $b_v$ bytes for each index value). Proton history data is generated by firing many imaging protons from each of a number of different angles. Again assuming near-linear trajectories the upper limit of voxels through which a single proton will pass can be reasonably approximated from the length of the diagonal ($l_d$) through the voxel space cube[1] (i.e., $l_d = \sqrt{V_h^2 + V_w^2 + V_d^2}$). Proton histories are evaluated at a resolution (i.e., step size s) that is determined by the desired imaging resolution and the MLP oversampling rate (i.e., $$s = \frac{V_T}{V_s}).$$

In addition to identifying those voxels through which protons pass, it has been shown that the quality of the final image can be improved by also recording an estimate of the proton path's chord length through each voxel (i.e., as opposed to simply identifying those voxels that were "touched"). Initially, we choose to compute an estimate the chord length, a floating point number, as a function of the voxel cube dimensions ($V_h$, $V_w$, $V_d$) and the firing angle. Without assuming anything regarding how the proton histories will be partitioned over the set of worker processes (e.g., a worker may receive all histories from a single firing angle or from many, or all, firing angles) a simple memory layout that "connects" a chord length and the angle that produced it to the voxel indices of the protons fired from that angle is to maintain a vector of chord lengths and two additional vectors in tandem as follows;

chord lengths—This is a vector of floats that records the computed chord length for each discrete firing angle (i.e., length=$I_a$).

firing angle index—This is a vector of integer indices into the first vector of chord lengths that records the angle from which each proton history was fired (i.e., length=$H_w$).

voxel index array—This is a vector of pointers where each proton history points to the vector of voxel indices (estimated length $l_d$) the proton "touched" on its path (i.e., length=$H_w$).

Under these approximations and simple memory layout scheme, an upper limit approximation of the memory needed to store the MLP voxels and their chord lengths ($MLP_m$) for each worker is $$MLP_m = I_a f + H_w \left\{ b_{Ia} + p + \left( \left\lceil \frac{l_d}{s} \right\rceil + 1 \right) b_v \right\} \quad (3)$$

$$= I_a f + H_w \left\{ \left( \left\lceil \frac{\lceil \log_2 I_a \rceil}{8} \right\rceil \right) + p + \left( \left\lfloor \frac{\sqrt{V_h^2 + V_w^2 + V_d^2}}{\frac{V_T}{V_s}} \right\rfloor + 1 \right) \right.$$

$$\left. \left( \left\lceil \frac{\lceil \log_2 V \rceil}{8} \right\rceil \right) \right\}$$

$$= I_a f + H_w \left\{ \left( \left\lceil \frac{\lceil \log_2 I_a \rceil}{8} \right\rceil \right) + p + \left( \left\lfloor \frac{V_s \sqrt{V_h^2 + V_w^2 + V_d^2}}{V_T} \right\rfloor + 1 \right) \right.$$

$$\left. \left( \left\lceil \frac{\lceil \log_2 \left( \left\lceil \frac{V_h V_w V_d}{V_T^3} \right\rceil \right) \rceil}{8} \right\rceil \right) \right\}$$

[1] In practice MLP evaluations will start and end with the entry and exit 3-tuples <x, y, z> generated from the space carving pre-processing of the input.

Solution Vector. The solution vector is an array of floats whose length is determined by the number of voxels V. We note that each worker maintains its own copy of the entire solution vector, and so, the memory needed to store the solution vector ($V_m$) in each worker is $$V_m = Vf = \left( \left\lceil \frac{V_h V_w V_d}{V_r^3} \right\rceil \right) f \quad (4)$$

Histories per worker. Each worker, including the foreman, must have enough space to store each of the above memory components, however, we note that once the input has been processed its memory may be re-used for the solution vector.

$$IED_m + MLP_m + MAX(I_m, V_m) \le M \quad (5)$$

Re-writing inequality (5) we see that we can compute the maximum number of histories each worker can process, $H_w$, as constrained by their memory M as follows:

$$\underbrace{H_w f}_{IED_m} + I_a f + H_w \left\{ \left( \left\lceil \frac{\lceil \log_2 I_a \rceil}{8} \right\rceil \right) + p + \left( \left\lfloor \frac{2\sqrt{V_h^2 + V_w^2 + V_d^2}}{V_r} \right\rfloor + 1 \right) \left( \left\lceil \frac{\lceil \log_2 \left( \left\lceil \frac{V_h V_w V_d}{V_r^3} \right\rceil \right) \rceil}{8} \right\rceil \right) \right\}}_{MLP_m} +$$

$$MAX \left( \underbrace{H_w \left[ 4 \left( \left\lceil \frac{\lceil \log_2 \frac{P_h}{P_r} \rceil}{8} \right\rceil + \left\lceil \frac{\lceil \log_2 \frac{P_w}{P_r} \rceil}{8} \right\rceil \right) + 3f \right] + \left\lceil \frac{V_h V_w V_d}{V_r^3} \right\rceil}_{I_m}, \underbrace{\left( \left\lceil \frac{V_h V_w V_d}{V_r^3} \right\rceil \right) f}_{V_m} \right) \le M \quad (6)$$

Number of processes. The number of voxels V and the number of protons per voxel $V_p$ tells us how many input proton histories there will be in all. That, when combined with maximum number of histories each worker can process as constrained by their memory, $H_w$, tells us how many worker processes we will need for to solve the problem which we denote P.

$$P = \left( \left\lceil \frac{V_p V}{H_w} \right\rceil \right) \quad (7)$$

4 Case Study

We compute here $H_w$ and P using the following values:
$P_h$, $P_w$=20 cm
$P_T$=0.238 mm
$I_a$=180
$V_h$, $V_w$, $V_d$=20 cm,
$V_T$=1 mm $V_S$=2
$V_p$=10
M=2 GB
f,p=4 bytes Substituting those values into inequality (6) we get[2]

$$180(4) + H_w \left\{ \left( \left\lceil \frac{\lceil \log_2 180 \rceil}{8} \right\rceil \right) + 4 + \quad (8)$$

$$\underbrace{\frac{4H_w}{IED_m} + \left( \left\lfloor \frac{2\sqrt{3(20^2)}}{.1} \right\rfloor + 1 \right) \left( \left\lceil \frac{\lceil \log_2 \left( \left\lceil \frac{20^3}{.1^3} \right\rceil \right) \rceil}{8} \right\rceil \right) \right\}}_{MLP_m} +$$

$$MAX \left( \underbrace{H_w \left[ 4 \left( \left\lceil \frac{\lceil \log_2 \frac{20}{.0238} \rceil}{8} \right\rceil + \left\lceil \frac{\lceil \log_2 \frac{20}{.0238} \rceil}{8} \right\rceil \right) + 3(4) \right] + \left\lceil \frac{20^3}{.1^3} \right\rceil}_{I_m}, \right.$$

$$\left. \underbrace{\left( \left\lceil \frac{20^3}{.1^3} \right\rceil \right) 4}_{V_m} \right) =$$

$$\underbrace{\frac{4H_w}{IED_m} + \underbrace{720 + H_w\{1 + 4 + (693)(4)\}}_{MLP_m} + MAX \left( \frac{28H_w + 8x10^6}{I_m}, \frac{32x10^6}{V_m} \right) =$$

$$2{,}781 \, H_w + 720 + MAX(28 H_w + 8x10^6, 32x10^6) \le 2 \, GB$$

Case I $28H_w + 8 \times 10^6 \ge 32 \times 10^6$: Rewriting inequality (8)

$$2{,}781 H_w + 720 + 28 H_w + 8x10^6 \le 2 \, GB$$

$$H_w \le \frac{2 \, GB - 720 - 8x10^6}{2{,}809}$$

$$H_w \le 761{,}652.9$$

Case II $28H_w + 8 \times 10^6 < 32 \times 10^6$: Rewriting inequality (8)

$$2{,}781 H_w + 720 + 32x10^6 \le 2 \, GB$$

$$H_w \le \frac{2 \, GB - 720 - 32x10^6}{2{,}781}$$

$$H_w \le 760{,}691.5$$

Since the memory required to store the solution under Case II $V_m = 32 \times 10^6$ is greater than the amount of memory to store the input $I_m = 28H_w + 8 \times 10^6 \approx 29 \times 10^6$ we use the value $H_w = 760{,}692$ computed under Case II. Applying that value to equation (7) we find that we need $$P = \left\lceil \frac{V_p V}{H_w} \right\rceil$$

$$= \left\lceil \frac{80,000,000}{760,692} \right\rceil$$

$$= 106$$

²Rounded $$\left(\left\lceil \frac{\left\lceil \log_2\left(\left\lceil \frac{20^3}{.1^3} \right\rceil\right) \right\rceil}{8} \right\rceil\right)$$

up from 3 to 4 so that value can be stored in int.

Appendix—for Spreadsheet

From inequality (6) we solve for $H_w$ under the two following cases:

Case I Solving for $H_w$ in (6) assuming $I_m \geq V_M$:

$$\underbrace{\frac{H_w f}{IED_m} + I_a f + H_w \left\{\left(\left\lceil \frac{\lceil \log_2 I_a \rceil}{8} \right\rceil\right) + p + \left(\left\lceil \frac{V_s \sqrt{V_h^2 + V_w^2 + V_d^2}}{V_r} \right\rceil + 1\right)\left(\left\lceil \frac{\left\lceil \log_2\left(\left\lceil \frac{V_h V_w V_d}{V_r^3} \right\rceil\right) \right\rceil}{8} \right\rceil\right)\right\} + \underbrace{H_w \left[4\left(\left\lceil \frac{\left\lceil \log_2 \frac{P_h}{P_r} \right\rceil}{8} \right\rceil + \left\lceil \frac{\left\lceil \log_2 \frac{P_w}{P_r} \right\rceil}{8} \right\rceil\right) + 3f\right] + \left\lceil \frac{V_h V_w V_d}{V_r^3} \right\rceil}_{I_m} \leq M}_{MLP_m}$$

$$H_w\left[f + \left\{\left(\left\lceil \frac{\lceil \log_2 I_a \rceil}{8} \right\rceil\right) + p + \left(\left\lceil \frac{V_s \sqrt{V_h^2 + V_w^2 + V_d^2}}{V_r} \right\rceil + 1\right)\left(\left\lceil \frac{\left\lceil \log_2\left(\left\lceil \frac{V_h V_w V_d}{V_r^3} \right\rceil\right) \right\rceil}{8} \right\rceil\right)\right\} + \left[4\left(\left\lceil \frac{\left\lceil \log_2 \frac{P_h}{P_r} \right\rceil}{8} \right\rceil + \left\lceil \frac{\left\lceil \log_2 \frac{P_w}{P_r} \right\rceil}{8} \right\rceil\right) + 3f\right]\right] \leq M - I_a f - \left\lceil \frac{V_h V_w V_d}{V_r^3} \right\rceil$$

$$\frac{M - I_a f - \left\lceil \frac{V_h V_w V_d}{V_r^3} \right\rceil}{\left[4f + \left(\left\lceil \frac{\lceil \log_2 I_a \rceil}{8} \right\rceil\right) + p + \cdots \right]} > H_w$$

or expressed using more convenient notation $$\frac{M - I_a f - V}{4f + b_{Ia} + p + \left(\left\lceil \frac{V_s(I_d)}{V_r} \right\rceil + 1\right) b_v + 4(b_{ph} + b_{pw})} > H_w \quad (9)$$

Substituting the parameters from section 4 we compute $H_w$ as follows:

$$\frac{2\,GB - (180)(4) - \left\lceil \frac{20^3}{.1^3} \right\rceil}{\left[4(4) + \left(\left\lceil \frac{\lceil \log_2 180 \rceil}{8} \right\rceil\right) + 4 + \left(\left\lceil \frac{2\sqrt{3(20^2)}}{.1} \right\rceil + 1\right)\left(\left\lceil \frac{\left\lceil \log_2\left(\left\lceil \frac{(20)^3}{.1^3} \right\rceil\right) \right\rceil}{8} \right\rceil\right) + 4\left(\left\lceil \frac{\left\lceil \log_2 \frac{20}{.0238} \right\rceil}{8} \right\rceil + \left\lceil \frac{\left\lceil \log_2 \frac{20}{.0238} \right\rceil}{8} \right\rceil\right)\right]} > H_w$$

$$\frac{2,139,482,928}{[16 + (1) + 4 + (692 + 1)(4) + 4(2 + 2)]} > H_w$$

$$761,652.9 > H_w$$

Case II Solving for $H_w$ in (6) assuming $I_m < V_M$:

$$\frac{\frac{H_w f}{IED_m} + I_a f + H_w \left\{ \left( \left\lceil \frac{\lceil \log_2 I_a \rceil}{8} \right\rceil \right) + p + \left( \left\lfloor \frac{V_s \sqrt{V_h^2 + V_w^2 + V_d^2}}{V_r} \right\rfloor + 1 \right) \left( \left\lceil \frac{\left\lfloor \log_2 \left( \left\lceil \frac{V_h V_w V_d}{V_r^3} \right\rceil \right) \right\rfloor}{8} \right\rceil \right) \right\}}{MLP_m} +$$

$$\frac{\left( \left\lceil \frac{V_h V_w V_d}{V_r^3} \right\rceil \right) f}{V_m} \le M$$

$$H_w \left\{ f + \left( \left\lceil \frac{\lceil \log_2 I_a \rceil}{8} \right\rceil \right) + p + \left( \left\lfloor \frac{V_s \sqrt{V_h^2 + V_w^2 + V_d^2}}{V_r} \right\rfloor + 1 \right) \left( \left\lceil \frac{\left\lfloor \log_2 \left( \left\lceil \frac{V_h V_w V_d}{V_r^3} \right\rceil \right) \right\rfloor}{8} \right\rceil \right) \right\} \le$$

$$M - I_a f - \left( \left\lceil \frac{V_h V_w V_d}{V_r^3} \right\rceil \right) f$$

$$\frac{M - \left\{ I_a + \left( \left\lceil \frac{V_h V_w V_d}{V_r^3} \right\rceil \right) \right\} f}{f + \left( \left\lceil \frac{\lceil \log_2 I_a \rceil}{8} \right\rceil \right) + p + \left( \left\lfloor \frac{V_s \sqrt{V_h^2 + V_w^2 + V_d^2}}{V_r} \right\rfloor + 1 \right) \left( \left\lceil \frac{\left\lfloor \log_2 \left( \left\lceil \frac{V_h V_w V_d}{V_r^3} \right\rceil \right) \right\rfloor}{8} \right\rceil \right)} > H_w$$

or expressed using more convenient notation $$\frac{M - (I_a + V) f}{f + b_{Ia} + p + \left( \left\lfloor \frac{V_s (l_d)}{V_r} \right\rfloor + 1 \right) b_v} > H_w \quad (10)$$

Substituting the parameters from section 4 into (10) we again compute $H_w$ as follows[3]

$$\frac{2 \, GB - \left\{ 180 + \left( \left\lceil \frac{20^3}{.1^3} \right\rceil \right) \right\} 4}{4 + \left( \left\lceil \frac{\lceil \log_2 180 \rceil}{8} \right\rceil \right) + 4 + \left( \left\lfloor \frac{2\sqrt{3(20^2)}}{.1} \right\rfloor + 1 \right) \left( \left\lceil \frac{\left\lfloor \log_2 \left( \left\lceil \frac{20^3}{.1^3} \right\rceil \right) \right\rfloor}{8} \right\rceil \right)} > H_w$$

$$\frac{2,115,482,928}{4 + (1) + 4 + (693)(4)} > H_w$$

$$760,691.5 > H_w$$

[3] Rounded $$\left( \left\lceil \frac{\left\lfloor \log_2 \left( \left\lceil \frac{20^3}{.1^3} \right\rceil \right) \right\rfloor}{8} \right\rceil \right)$$

up from 3 to 4 so that value can be stored in int.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A proton computed tomography (pCT) detector system, comprising: two tracking detectors in sequence on a first side of an object to be imaged, two tracking detectors in sequence on an opposite side of the object to be imaged, a calorimeter, and a computer cluster, wherein said tracking detectors include plastic scintillation fibers.

2. The pCT detector system of claim 1, wherein said plastic scintillation fibers have a 1 mm diameter.

3. The pCT detector system of claim 1, wherein said plastic scintillation fibers are packed in a row covering the full area of an imaging field.

4. The pCT detector system of claim 3, wherein said imaging field is 27 by 36 cm.

5. The pCT detector system of claim 1, wherein said plastic scintillation fibers are arranged in a plane, and said tracking detectors include at least two stacked planes.

6. The pCT detector system of claim 5, wherein said two stacked planes are oriented in X and Y directions.

7. The pCT detector system of claim 6, further including a thin foam-like material in between said two stacked planes.

8. The pCT detector system of claim 1, wherein said plastic scintillation fibers have a cross-sectional shape chosen from the group consisting of a square, circle, and hexagon.

9. The pCT detector system of claim 1, wherein two plastic scintillation fibers are attached to each SiPM.

10. The pCT detector system of claim 1, wherein one plastic scintillation fiber is attached to each SiPM.

11. The pCT detector system of claim 1, wherein said tracking detectors further include support means for supporting the fibers and SiPMs.

12. The pCT detector system of claim 1, wherein said plastic scintillation fibers are made of polystyrene with cladding of PMMA (Poly(methyl methacrylate)).

13. The pCT detector system of claim 1, wherein said calorimeter includes silicon photomultipliers (SiPMs) attached to wavelength shifting (WLS) fibers.

14. The pCT detector system of claim 13, wherein said calorimeter includes a stack of scintillator plates, and wherein each scintillator plate includes one SiPM and one WLS.

15. The pCT detector system of claim 1, wherein said computer cluster further includes analyzing means for analyzing the protons detected by the tracking detectors and calorimeter.

16. The pCT detector system of claim 15, wherein said analyzing means includes a foreman computer and multiple worker computers.

17. The pCT detector system of claim 1, further including a rotating stage for rotating the object, and wherein said tracking detectors are inside enclosures.

18. A method of imaging an object, including the steps of:
emitting protons from a source through two tracking detectors, through and around the object, and through two opposite tracking detectors; detecting energy of the protons with a calorimeter; and imaging the object; and
wherein the tracking detectors include plastic scintillation fibers packed in a row covering the full area of an imaging field and include silicon photomultipliers.

19. The method of claim 18, wherein said emitting step further includes the step of determining a position of the protons at the two tracking detectors and two opposite tracking detectors.

20. The method of claim 18, wherein said determining step further includes the step of measuring the protons in X and Y planes of the tracking detectors.

21. The method of claim 18, wherein the calorimeter includes silicon photomultipliers attached to wavelength shifting (WLS) fibers.

22. A method of imaging an object, including the steps of:
emitting protons from a source through two tracking detectors, through and around the object, and through two opposite tracking detectors; detecting energy of the protons with a calorimeter; and imaging the object; and
wherein said imaging step includes analyzing data acquired from the tracking detectors and calorimeter on a cluster of multiple computers and graphic processing units with a Message Passing Interface (MPI) standard.

23. The method of claim 22, wherein said imaging step includes compact memory representation and solving an entire 3D image space at a single time.

24. The method of claim 22, further including the steps of a foreman computer distributing equal amounts of proton histories to multiple worker computers and the foreman computer, computing an Integrated Electron Density (IED) and Most Likely Path (MLP), solving for a solution vector and storing on computer readable memory, sending copies of the solution vector to the foreman computer, combining the solution vectors of the worker computers and the foreman computer and storing the combined solution vector on computer readable media, testing the combined solution vector, and if the combined solution vector is done, producing an image of the object.

25. The method of claim 24, wherein if the combined solution vector is not done, transmitting the combined solution vector to the worker computers, and repeating the distributing, computing, solving, sending, combining, testing steps until the combined solution vector is done, and producing an image of the object.

* * * * *